United States Patent [19]
Logeman

[11] Patent Number: 5,947,996
[45] Date of Patent: Sep. 7, 1999

[54] YOKE FOR SURGICAL INSTRUMENT

[75] Inventor: John Logeman, Park Ridge, Ill.

[73] Assignee: Medicor Corporation, Vernon Hills, Ill.

[21] Appl. No.: 08/880,212

[22] Filed: Jun. 23, 1997

[51] Int. Cl.$^6$ ................................................. A61B 17/28
[52] U.S. Cl. ........................... 606/205; 606/174; 600/564
[58] Field of Search ..................... 606/51, 52, 1, 606/174, 205–210; 600/564

[56] References Cited

U.S. PATENT DOCUMENTS

| | | |
|---|---|---|
| 2,068,721 | 12/1937 | Wappler et al. . |
| 4,041,952 | 8/1977 | Morrison, Jr. et al. . |
| 4,076,028 | 2/1978 | Simmons . |
| 4,512,343 | 4/1985 | Falk et al. . |
| 4,732,149 | 3/1988 | Sutter . |
| 4,887,612 | 12/1989 | Esser et al. . |
| 4,957,498 | 9/1990 | Caspari et al. . |
| 5,030,218 | 7/1991 | Alexander . |
| 5,147,357 | 9/1992 | Rose et al. . |
| 5,152,774 | 10/1992 | Schroeder . |
| 5,330,471 | 7/1994 | Eggers . |
| 5,336,238 | 8/1994 | Holmes et al. ........................ 606/205 |
| 5,445,638 | 8/1995 | Rydell et al. . |
| 5,458,598 | 10/1995 | Feinberg et al. . |
| 5,472,443 | 12/1995 | Cordis et al. . |
| 5,496,317 | 3/1996 | Goble et al. . |
| 5,540,684 | 7/1996 | Hassler, Jr. . |
| 5,549,606 | 8/1996 | McBrayer et al. . |
| 5,556,416 | 9/1996 | Clark et al. . |
| 5,558,671 | 9/1996 | Yates . |
| 5,722,988 | 3/1998 | Weisshaupt ........................... 606/205 |

FOREIGN PATENT DOCUMENTS 2106039  3/1994  Canada .

*Primary Examiner*—Michael Buiz
*Assistant Examiner*—William Lewis
*Attorney, Agent, or Firm*—Olson & Hierl, Ltd.

[57] ABSTRACT

A yoke suitable for connecting an end effector to a manipulator shaft therefor in a surgical instrument. The yoke includes an elongated hollow stem which defines a central passageway for the manipulator shaft and a plurality of barbed flexible leaves unitary with the stem. Each of the leaves terminates in a sphenoid barb portion. Adjacent barb portions define a substantially v-shaped slot therebetween which facilitates the compression and flexing of the leaves during the connection of the manipulator shaft to the surgical instrument.

19 Claims, 6 Drawing Sheets

YOKE FOR SURGICAL INSTRUMENT

TECHNICAL FIELD OF THE INVENTION

This invention relates to surgical instruments and, more particularly, to a yoke for electrosurgical instruments which facilitates the connection and separation of the manipulator shaft from the instrument for cleaning.

BACKGROUND OF THE INVENTION

Various types of electrosurgical endoscopic medical and surgical instruments are known in the art. These instruments typically include an elongated insulated instrument tube which houses an elongate manipulator shaft which is axially reciprocable within the tube by means of a handle or trigger-like actuating means. An end effector or surgical tool such as, for example, a forceps, a gripper, or a cutter, is coupled to the distal end of the manipulator shaft by a linkage which translates the axial movement of the shaft into a desired movement of the end effector.

As a result of the use of such instruments, it is normal for tissue or body fluid to be deposited upon and between any one of the various parts of the instrument including the tube, the shaft, the end effector, and its associated linkages. Some of such instruments known in the art include a "take-apart" shaft incorporating a yoke which allows the shaft to be disconnected and removed from the tube for sterilization and cleaning.

The present invention provides an improved yoke for coupling an end effector with its manipulator shaft which allows a user to simply and smoothly secure and remove the manipulator shaft from the instrument tube so that the shaft can be cleaned and sterilized separately from the tube or, alternatively, to allow the user to simply and quickly substitute different end effectors in the same instrument.

SUMMARY OF THE INVENTION

A yoke suitable for coupling an end effector, such as a gripper, to a manipulator shaft used in a surgical instrument. The yoke includes an elongated hollow stem which defines a central passageway for the manipulator shaft and a clevis unitary with the stem at one end of the stem. The yoke also includes a plurality of barbed, flexible leaves or legs unitary with the hollow stem. Each of the leaves terminates in a spheroid or wedge-shaped barb portion which surrounds the central passageway at the opposite end of the stem. Adjacent barb portions of the flexible leaves define therebetween a substantially v-shaped slot with the apex of the slot toward the stem.

In use, the yoke is operably coupled to the distal end of the manipulator shaft and extends into the distal end of an instrument tube. The barb portions guide the yoke into the instrument tube. Each of the barb portions includes a shoulder and opposed inwardly converging flat sides. The inwardly converging sides of adjacent barb portions define the v-shaped slot. Preferably, the v-shaped slot defined between adjacent barb portions is closed and the sides of adjacent barb portions abut each other when the yoke is respectively extended into and removed from the instrument tube to facilitate the flexing and compression of the leaves so that the manipulator shaft is easily and smoothly extended and removed from the instrument tube. The shoulder on each of the barb portions abuts against a shoulder in the interior of the instrument tube to secure the manipulator shaft within the instrument tube.

The manipulator shaft additionally includes a neck having an interior circumferential cavity. To disengage the manipulator shaft from the instrument tube, the barb portions of the leaves of the yoke are wedged into the neck cavity to cause the flexing and compression of the leaves which, in turn, causes the disengagement of the shoulder on each of the barb portions from the shoulder in the interior of the instrument tube to disengage the manipulator shaft from the instrument tube.

Preferably, the v-shaped slot defined between adjacent barb portions is closed and the inwardly converging sides of adjacent barb portions advantageously abut each other when the barb portions are wedged into the neck cavity of the manipulator shaft so as to facilitate the flexing and compression of the leaves thus facilitating the smooth and effortless disengagement of the manipulator shaft from the instrument tube.

Other features and advantages of the present invention will become readily apparent from the following detailed description, the appended drawings, and the accompanying claims.

DESCRIPTION OF THE PREFERRED EMBODIMENT

Figure 1:
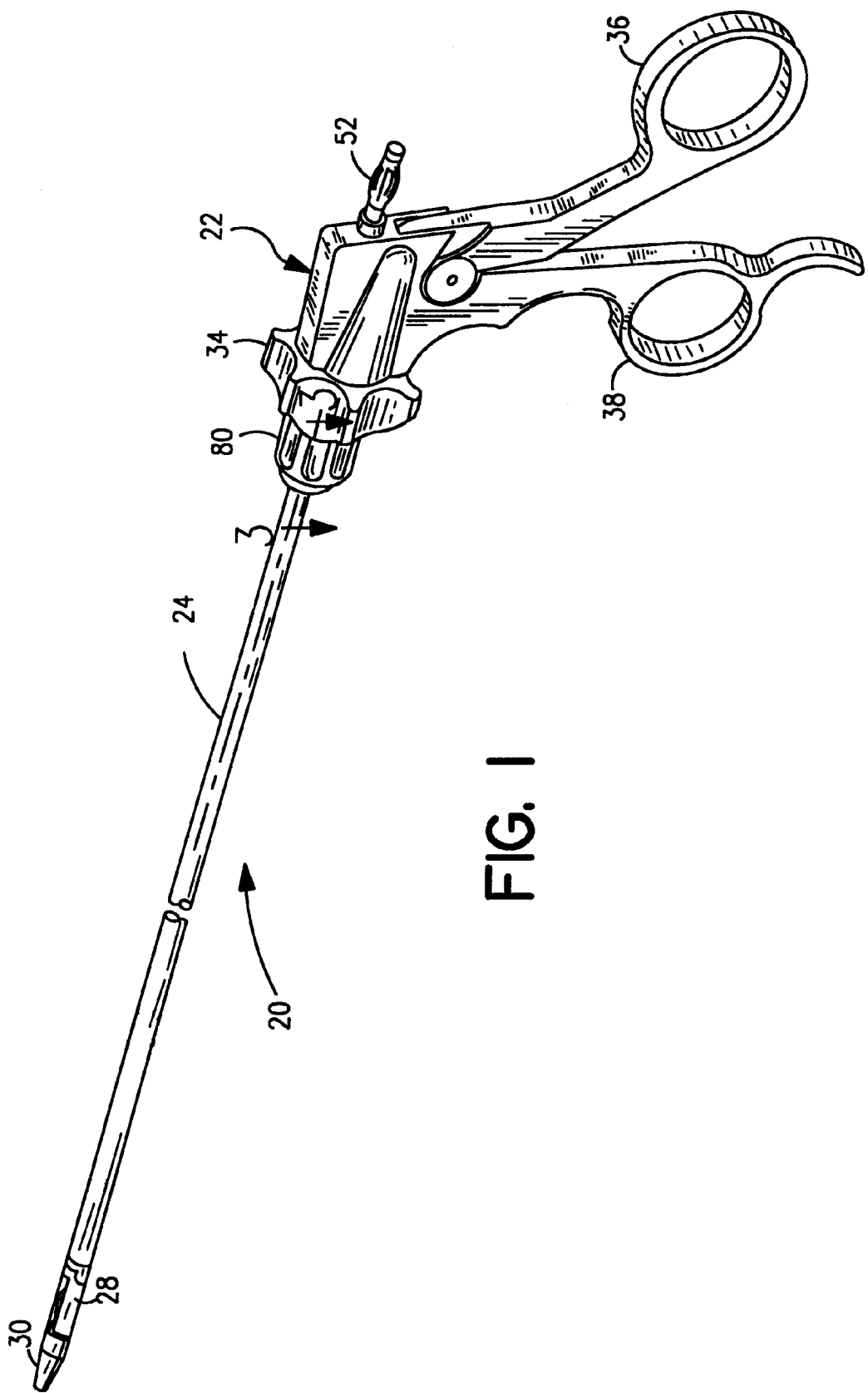
FIG. 1 is a perspective view of an endoscopic surgical instrument embodying the principles of the present invention.

The invention disclosed herein is, of course, susceptible of embodiment in many different forms. Shown in the drawings and described hereinbelow in detail are preferred embodiments of the invention. It is to be understood, however, that the present disclosure is an exemplification of the principles of the invention and does not limit the invention to the illustrated embodiments.

For ease of description, an endoscopic medical instrument embodying the present invention is described hereinbelow in its horizontal operating position as shown in the accompanying drawings and terms such as upper, lower, vertical, etc., will be used herein with reference to this position as shown in the drawings.

The Figures show details of the instrument's mechanical elements that are known in the art and that will be recognized by those skilled in the art as such. The detailed descriptions of such elements are not necessary to an understanding of the invention. Accordingly, such elements are herein represented only to the degree necessary to aid an understanding of the features of the present invention.

It is further understood that the yoke of the present invention is not limited to use in the endoscopic surgical instrument described and depicted herein but rather is usable in any surgical instrument which incorporates a removable shaft.

Figure 2:
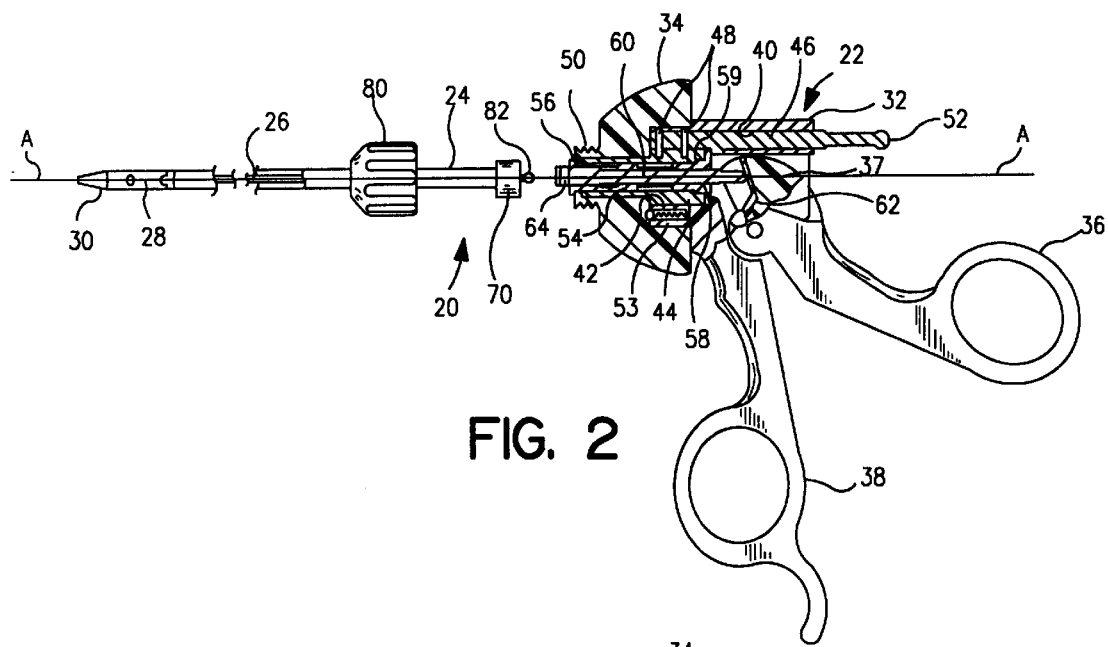
FIG. 2 is an enlarged, partial side elevational view of the instrument of FIG. 1 with portions of handle and instrument tube broken away and in cross-section.

Referring now the drawings, and more particularly, to FIGS. 1 and 2, there is shown therein an electrosurgical endoscopic instrument 20 constructed in accordance with the present invention.

Instrument 20 includes a handle member 22, an elongate insulated instrument tube 24, an elongate manipulator shaft 26 extending through the tube 24, a yoke 28 coupled or connected to and surrounding the distal end of the manipulator shaft 26, and an instrument end effector in the form of a forceps or gripper 30 operably connected or coupled to both the distal end of the manipulator shaft 26 and the yoke 28.

Handle member 22, which is preferably made of plastic, has a pistol-like configuration and includes a body portion 32, a knurled rotatable knob 34 mounted at the front of the body portion 32, a thumb handle 36 including a rocker arm 37 depending from and pivotable about the body portion 32, and a fixed finger handle 38 depending from and unitary with the body portion 32.

As shown in FIG. 2, body portion 32 includes a inner cavity 40 which, in part, defines a channel 42 extending through body portion 32 along a longitudinal axis A. Inserts 44 and 46, which are preferably made of stainless steel, fill the cavity 40. Insert 44, which is generally tubular and hollow, extends longitudinally through the channel 42 along axis A. Insert 46, which is solid, abuts the top of the distal end of insert 44 and extends rearwardly therefrom. A pair of pins 48 connect the two inserts 44 and 46 together. Insert 46 terminates in an electrical jack pin 52 for use of the instrument in its electro-cautery applications.

Knob 34, which includes a unitary threaded stem 50, surrounds and is journalled for rotation on the portion of tubular insert 44 extending away and out of body portion 32. A spring detent mechanism 53 in the body portion 32 of handle member 22 is operably associated with the knob 34 to hold the knob 34 in its selected rotated position. Knob 34 is held on the tubular insert 44 by an elongate tubular member 54 which is fitted and snapped within the interior of tubular insert 44. A radial shoulder 56 on the distal end of member 54 abuts against the radial face of the stem 50 of knob 34 to hold the knob 34 on the tubular insert 44. The proximal end of member 54 includes a shouldered wedge-shaped tip 58 which is snappingly secured against a shoulder 59 in the interior of tubular insert 44. Member 54 is also preferably made of stainless steel.

An elongate connector rod 60 extends through the member 54 and the handle body portion 32 between the threaded stem 50 of knob 34 and the rocker arm 37 of thumb handle 36. One end of connector rod 60 is seated in a cradle 62 in the rocker arm 37 of thumb handle 36. The opposite end of connector rod 60 includes a ball receiving socket 64. Connector rod 60, which is also preferably made of stainless steel, is mounted for reciprocal longitudinal movement within member 54 in response to the pivotal movement of thumb handle 36.

Figure 11:
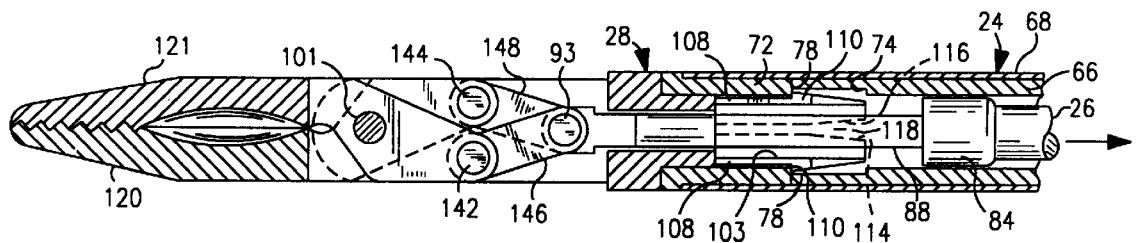
FIG. 11 is a partial cross-sectional view of the yoke and manipulator shaft secured in the instrument tube and with end effector jaws in their closed configuration.

Referring to FIGS. 2 and 11, instrument tube 24 includes an elongate, preferably stainless steel, tubular core 66 surrounded by a layer of insulating material 68 such as ceramic or the like. Tube 24 includes a proximal neck 70. Tube 24 also includes a tubular distal end cap 72 and an interior cavity 74 adjacent the end cap 72. Interior cavity 74 has a diameter greater than the interior diameter of tube 24. End cap 72 includes diametrically opposed semi-spherically shaped tabs 76 extending unitarily outwardly from a radial end wall thereof (FIG. 14) and is welded to the distal end of tube 24 during the manufacture of the instrument after the cavity 74 has been formed in the tube 24. End cap 72 and cavity 74 in combination define a shoulder 78 in the interior distal end of tube 24.

A threaded knurled knob or collar 80 surrounds the tube 24 for coupling the tube 24 to the handle member 22.

Figure 5:
FIG. 5 is a side elevational view of the manipulator shaft coupled to a gripper.
Figure 13:
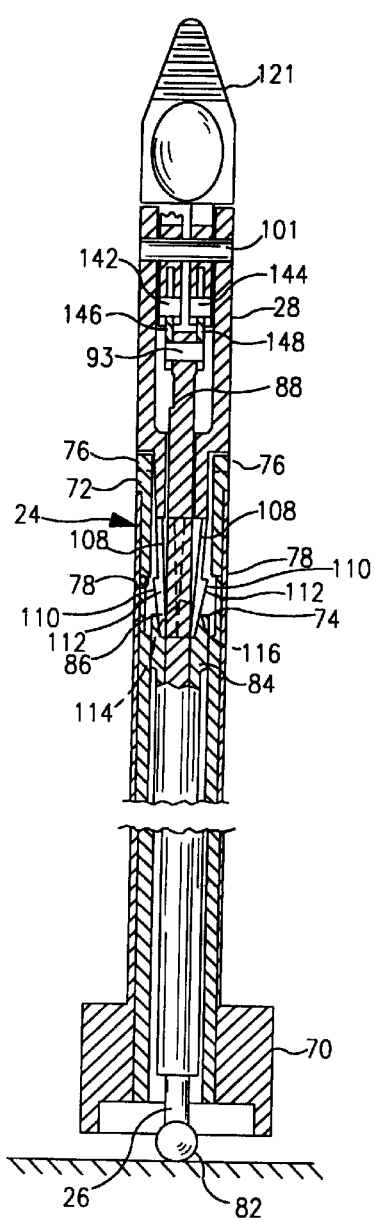
FIGS. 13 and 14 are partial cross-sectional views depicting the procedure for disengaging the manipulator shaft from the instrument tube.

As shown in FIGS. 5, 11 and 13, manipulator shaft 26, which is also preferably made of stainless steel, includes a proximal end with a unitary ball joint 82. The distal end of manipulator shaft 26 includes a neck 84 which is partially hollow so as to define an interior circumferential cavity 86 therein. A rod 88 extends outwardly from the interior of the neck 84. Rod 88 terminates in a unitary flat coupling member 90 having a circular aperture 92 for receiving a coupling pin 93.

Referring to FIGS. 6–9, yoke 28, which is also preferably made of stainless steel, includes a generally cylindrically shaped clevis or fork 94 having a generally cylindrical base 96 and two diametrically opposed and spaced apart generally semi-cylindrically shaped fingers 98 unitary with base 96 and extending longitudinally away from the base 96. The fingers 98 include aligned apertures 99 for receiving a coupling pin 101. Yoke 28 additionally includes an elongate tubular hollow stem 100 unitary with and extending from the base 96 in a direction opposite the fingers 98. Stem 100 defines a central generally cylindrical passageway 103 (FIGS. 10 and 11) for the rod 88 of manipulator shaft 26. The stem 100 has a diameter less than the diameter of the base 96 so as to define a radial shoulder 102 between the base 96 and the stem 100. A pair of opposed semi-spherically shaped grooves 104 are defined in the radial face of shoulder 102.

Figure 8:
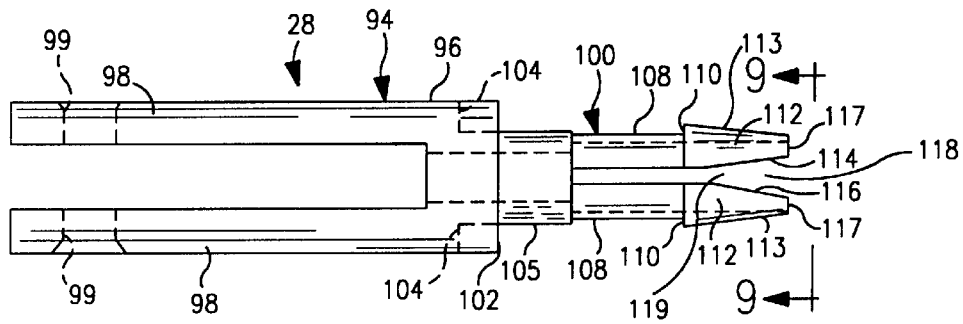
FIG. 8 is an enlarged side elevational view of the yoke of FIG. 7.
Figure 9:
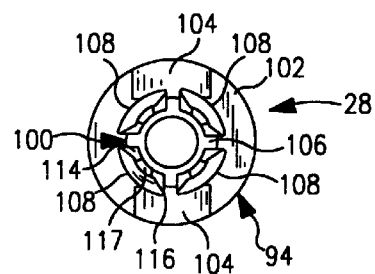
FIG. 9 is an end elevational view of the yoke taken along the plane 9—9 in FIG. 8.

Stem 100 includes a tubular hollow collar 105 unitary with the fork 94 and having a radial end face 106. Stem 100 further includes a plurality of barbed, flexible leaves or legs 108 extending longitudinally and circumferentially about the radial end face 106 of collar 105 in spaced-apart and adjacent relationship. Each of the legs 108 includes a shoulder 110 and a sphenoid, or wedge shaped, barb portion or tip 112 that extends outwardly from the shoulder 110 and surrounds the central passageway 103 at the other end of the stem 100. Each of the tips 112 includes a top surface 113 and opposed flat side surfaces 114 and 116 which all taper inwardly from the shoulder 110 and terminate into a flat peripheral curved end face 117. The tapered side surfaces 114 and 116 of adjacent barb portions 112 define therebetween a substantially v-shaped slot 118 having an apex 119 pointed in the direction of stem 100 (FIG. 8).

Each of the tapered side surfaces 114 and 116 tapers outwardly from end face 117 at an angle of about twenty degrees and extends toward stem 100 about three fourths the length of the respective tip 112. The taper angle can be varied as desired. The side surfaces 114 and 116 can extend anywhere from about one eighth the length of the respective tip 112 to about three fourths the length of the respective tip 112.

Figure 6:
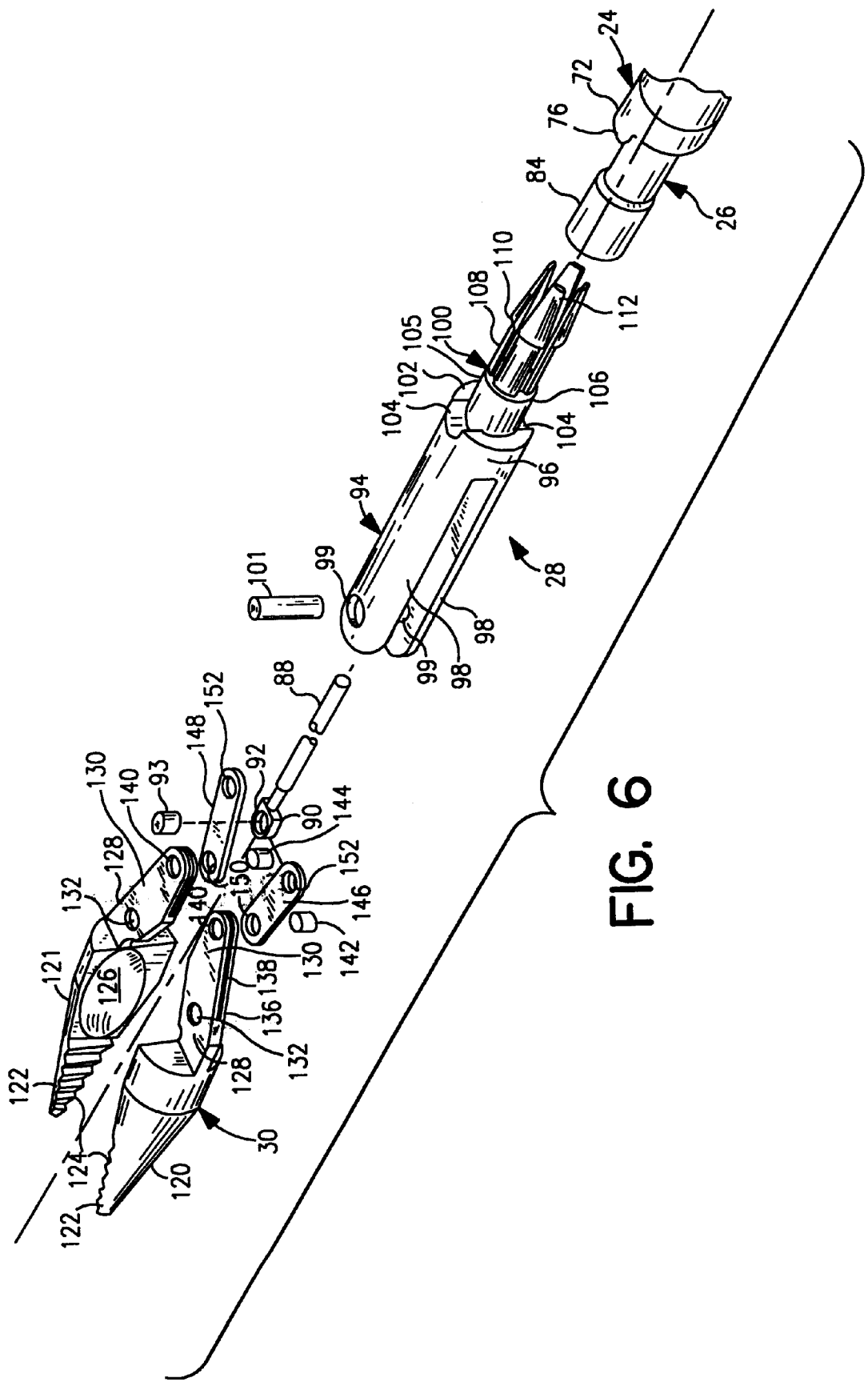
FIG. 6 is an enlarged exploded view of the instrument tube, the manipulator shaft, the yoke, and the end effector of the instrument of the present invention, with the instrument tube being broken away.
Figure 7:
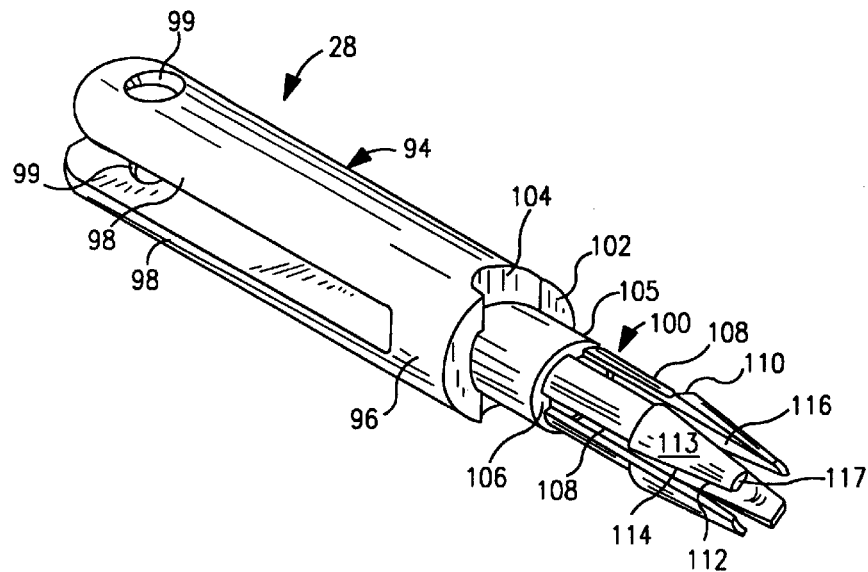
FIG. 7 is an enlarged perspective view of the yoke of the present invention.

The yoke 28 and end effector 30 are operably coupled to each other and the manipulator shaft 26. As shown in FIG. 6, end effector 30 includes two forceps jaws 120 and 121. Each of the jaws 120 and 121 includes a distal generally triangularly shaped gripper portion 122 having a series of teeth 124 for gripping tissue and a hemispherical cup 126 for collecting tissue. Each of the jaws 120 and 121 further includes a clevis portion 128 and a proximal tang 130 unitary with and aft of the clevis portion 128. Clevis portion 128 is provided with an axle hole 132 for receiving pin 101. Tang 130 is split into parallel and spaced-apart arms 136 and 138, each provided with an aperture 140 for receiving tang pins 142 and 144.

End effector 30 additionally includes two linking arms 146 and 148, each including opposed apertures 150 and 152 for receiving tang pins 142 and 144 and coupling pin 93 respectively.

End effector 30 is assembled and coupled to the yoke 28 and manipulator shaft 26 during the manufacturing process as described below. Initially, linking arms 146 and 148 are coupled to forceps jaws 120 and 121 respectively by inserting linking arms 146 and 148 between the tang arms 136 and 138 respectively until the aperture 150 in each of the linking arms 146 and 148 respectively is aligned with the apertures 140 in tang arms 136 and 138 respectively. Tang pins 142 and 144 are then inserted into the aligned apertures and spread with a riveting instrument.

Linking arms 146 and 148 are then brought together and placed on opposite sides of the coupling member 90 of connector rod 88 until the aperture 152 in each of the linking arms 146 and 148 is aligned with the aperture 92 in coupling member 90. Coupling pin 93 is then inserted into the aligned apertures and spread with a riveting instrument.

End effector 30 is then moved inwardly into the yoke 28 between the fingers 98 of fork 94 until the axle holes 132 in forceps jaws 120 and 121 respectively are aligned with the pin apertures 99 in fork fingers 98 and rod 88 has been fully extended through the passageway 103 in stem 100. Coupling pin 101 is then inserted through the aligned apertures and spread with a riveting instrument. The coupling of end effector 30 to the yoke 28 and the coupling of the yoke 28 to the shaft 26 is completed with the securement, as by welding or the like, of the end of rod 88 into the interior of the neck 84 of manipulator shaft 26.

Having described the various component parts of instrument 20, the manner in which the instrument 20 is assembled by a user and subsequently used will now be described.

Figure 4:
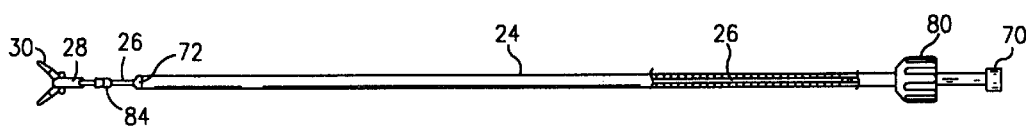
FIG. 4 is a side elevational view of the instrument tube and manipulator shaft with gripper of the present invention, with the tube shown in partial cross-section and the shaft partly extending from the tube.

Initially, manipulator shaft 26 is secured in the tube 24. First, the ball end of the manipulator shaft 26 shown in FIG. 5 is introduced into the tube 24 through the end cap 72. Shaft 26 is then slid and extended through the tube 24 as shown in FIG. 4 until the tips 112 of yoke 28 abut the opening of end cap 72. The tabs 76 on cap 72 are then aligned with the grooves 104 in the yoke 28 respectively and the yoke 28, guided by the wedge shaped tips 112 of legs 108, is then introduced and extended into the distal end of tube 24 as shown in FIG. 10.

Figure 10:
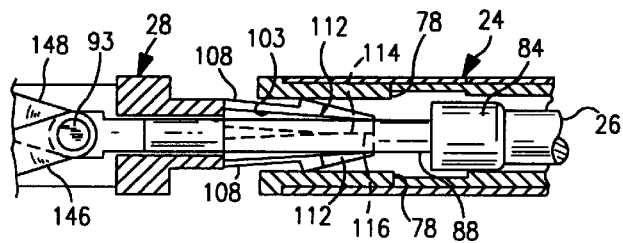
FIG. 10 is a partial cross-sectional view depicting the yoke and manipulator shaft positions while being inserted into the instrument tube.

Because the interior diameter of tube 24 is smaller than the diameter of the stem 100 on yoke 28, the legs 108 of yoke 28 are compressed into contact with the rod 88 of manipulator shaft 26 and into contact with each other as shown in FIG. 10 as stem 100 is extended into the distal end of tube 24 so as to define a frustoconically shaped passageway 103 in the interior of stem 100. Preferably, the v-shaped slot 118 between adjacent tips 112 is at least partially closed and the tapered sides 114 and 116 of the tips 112 of adjacent legs 108 at least partially abut each other as the stem 100 is extended into the tube 24. This feature is particularly advantageous because it allows the tips 112, and thus the flexible legs 108 of yoke 28 to be tightly compressed into contact with each other as the stem 100 is introduced into the tube 24. The tight compression, in turn, allows the stem 100 to be easily and smoothly guided and pushed through the distal end of tube 24.

Figure 12:
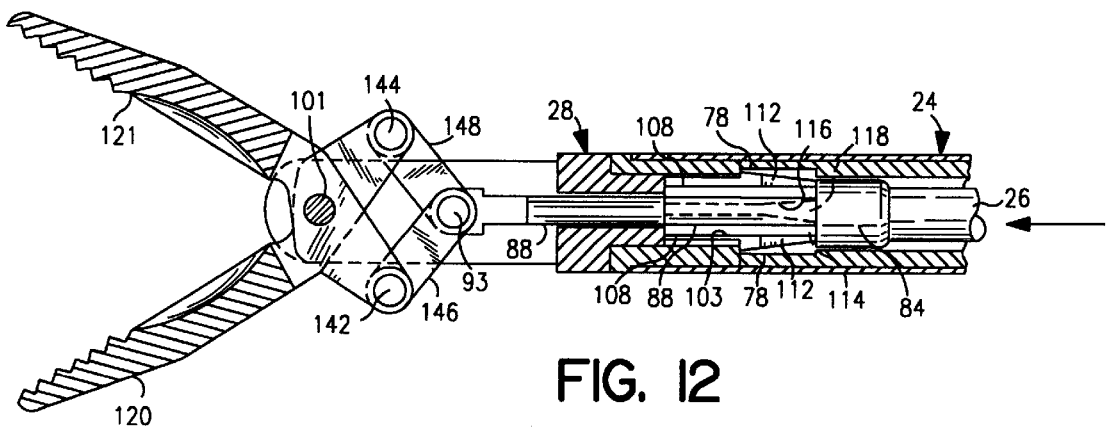
FIG. 12 is a partial cross-sectional view of the yoke and manipulator shaft secured in the instrument tube and with the end effector jaws in their open configuration.

The tube 24 and shaft 26 are then further brought together until the two parts are snapped together and the tabs 76 on cap 72 are received in the grooves 104 in yoke 28 as shown in FIGS. 11 and 12. The parts are snapped together as a result of the tips 112 of yoke 28 being slid into the cavity 74 in the interior of tube 24 which causes the legs 108 to spring and flex away from the rod 88 and causes the shoulder 110 on each of the tips 112 to abut and snap against the shoulder 78 in tube 24 thus securing the manipulator shaft 26 in the instrument tube 24.

Figure 3:
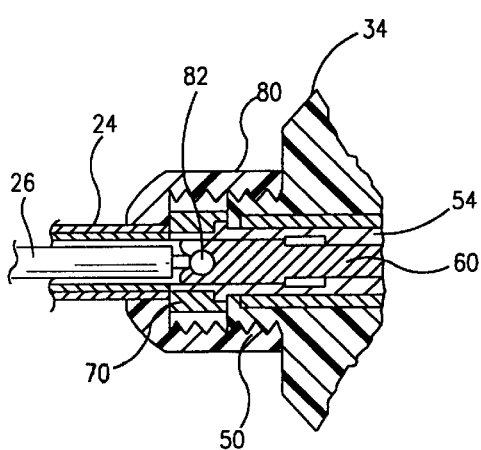
FIG. 3 is an enlarged, partial cross-sectional view, taken along the plane 3—3 in FIG. 1, of the connection between the instrument tube and the handle.

To secure the tube 24 to the handle member 22, tube 24 is initially brought into longitudinal alignment with axis A of handle member 22 (FIG. 2). Tube 24 and handle member 22 are then brought together and the ball 82 on shaft 26 is seated in the socket 64 in connector rod 60 (FIGS. 2 and 3).

Thumb handle 36 is subsequently depressed towards the finger handle 38 to cause the reciprocal movement of connector rod 60 into the handle member 22 which, in turn, moves the neck 70 of tube 24 longitudinally into abutting relationship against the stem 50 of knob 34. Collar 80 is then slid and threaded onto the stem 50 of knob 34 to secure the tube 24 to the handle member 22. Instrument 20 is then ready for use.

In use, the back and forth movement of thumb handle 36 is translated into the pivotal opening and closing of forceps jaws 120 and 121. As shown in FIG. 2, the retraction of thumb handle 36 away from the finger handle 38 causes the counter-clockwise rotation of rocker arm 37 on thumb handle 36 causing the forward reciprocal movement of connector 60 in handle member 22. This, in turn, causes the forward movement of shaft 26 in tube 24 which, as shown in FIG. 12, causes the forward reciprocal movement of rod 88 which, in turn, causes the separation of end effector linking arms 146 and 148 and finally the pivotal opening of jaws 120 and 121 about pin 101.

The movement of thumb handle 36 back towards the finger handle 38 causes the rearward reciprocal movement of connector rod 60 in handle member 22 which causes the rearward reciprocal movement of shaft 26 in tube 24 which causes the rearward reciprocal movement of rod 88. This causes the linking arms 146 and 148 to come back together as shown in FIG. 11 which, in turn, causes jaws 120 and 121 to pivot about pin 101 and close.

Those skilled in the art will appreciate that the length of manipulator shaft 26 in combination with the length of thumb handle 36 magnifies the force applied so that a relatively small force applied by the thumb of a practitioner results in a much stronger gripping force between jaws 120 and 121. It is also appreciated that rotation of the knob 34 rotates both the tube 24 and the end effector 30 about the longitudinal axis A of instrument 20. The ball 82 in the socket 64 of connector rod 60 allows the shaft 26 to rotate a full 360° with the tube 24 relative to the handle member 22 for precise alignment of the end effector while eliminating awkward wrist movements.

It is understood that, where desired to perform an electrocautery procedure, electrosurgical RP power can be applied to jack pin 52 on handle member 22 to provide resistive heating to jaws 120 and 121.

An advantage associated with instrument 20 as described above is that it can simply, quickly and smoothly be disassembled and separated into each of its component parts in essentially the same manner as it is assembled as described above so that each of the parts, i.e., the handle member 22, the instrument tube 24, and the manipulator shaft 26 can be individually cleaned and sterilized.

Tube 24 is separated from the handle member 22 by unscrewing the knob 80 from the knob 34 and then retracting the thumb handle 36 away from the finger handle 38 to cause the forward reciprocal movement of connector rod 60 so as to expose the ball 82 in the socket 64. An upward motion is then used at the base of the tube 24 to disengage the ball 82 from the socket 64 and separate the tube 24 from the handle member 22.

Figure 14:
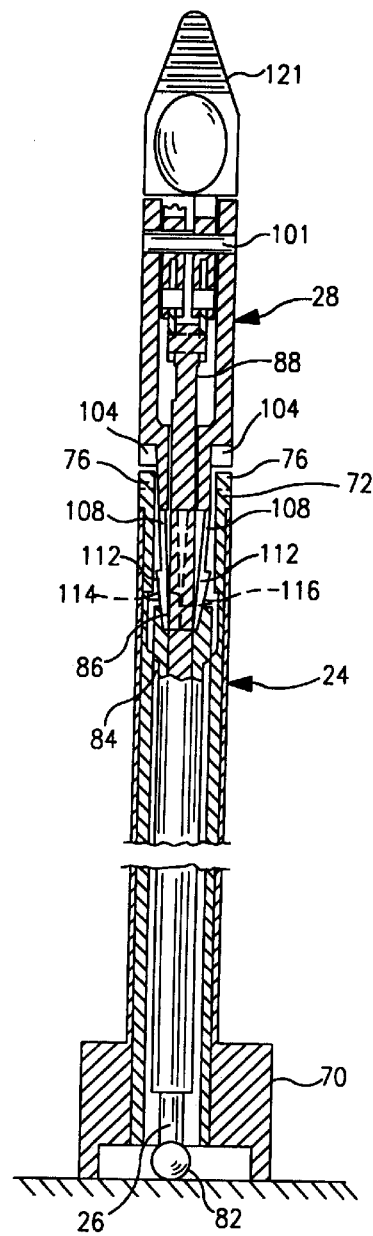

To remove the shaft 26 from the tube 24, tube 24 is placed in an upright vertical orientation as shown in FIG. 13 with the ball 82 of shaft 26 seated against a hard support surface. Tube 24 is then pressed firmly downwardly to snap the shaft 26 out of the tube 24 as shown in FIG. 14.

The disengagement occurs as a result of the downward movement of the tube 24 relative to the manipulator shaft 26 which initially causes the neck 84 of shaft 26 to move upwardly into contact with the legs 108 of yoke 28 as shown in FIG. 11. The further movement of the tube 24 relative to the shaft 26 then causes the wedging of the legs 108 of yoke 28 into the interior peripheral cavity 86 of the neck 84 of shaft 26 which, in turn, causes the flexing and compression of the legs 108 of yoke 28 into contact with each other and against the surface of rod 88.

As shown in FIG. 13, this compression causes the shoulder 110 on each of the tips 112 of legs 108 to flex radially inwardly away from the shoulder 76 in the tube 24 to disengage the yoke 28 from the tube 24. Once disengaged, the shaft 26 is slid out of the tube 24 as shown in FIG. 14.

The tapered sides 114 and 116 on each of the tips 112 of legs 108 which define the v-shaped slots 118 between adjacent tips 112 are particularly advantageous in the disengagement procedure because they allow the tips 112 to be firmly compressed and preferably abutted against each other as the tips 112 are wedged within the neck 84 of shaft 26 thus allowing the legs 108 to be tightly and firmly compressed against the rod 88 and each other which, in turn, allows the shoulder 110 on tips 112 to easily clear the shoulder 76 in tube 24 to disengage the yoke 28 from the tube 24. The tight compression also allows the shaft 26 to be easily and smoothly slid out of the tube 24.

Another advantage of the quick connect and disconnect yoke of the present invention is that a variety of different end-effectors including, but not limited to, needle holders, dissectors, cutters and scissors can quickly and easily be substituted for the forceps end-effector described and depicted in the drawings.

From the foregoing, it will be observed that numerous modifications and variations can be effected with departing from the true spirit and scope of the novel concepts of the present invention. It will be appreciated that the present disclosure is intended as an exemplification of the invention, and is not intended to limit the invention to the specific embodiments illustrated. The disclosure is intended to cover by the appended claims all such modifications as fall within the scope of the claims.

I claim:

1. A yoke suitable for connecting an end effector to a manipulator shaft therefor in a surgical instrument which yoke comprises:

an elongated hollow stem defining a central passageway for the manipulator shaft;

a clevis unitary with the stem at one end of the stem; and plural, barbed, flexible leaves unitary with the hollow stem, each terminating in a sphenoid barb portion, and surrounding the central passageway at the opposite end of the stem;

adjacent barb portions of the flexible leaves defining therebetween a substantially v-shaped slot with the apex of the slot toward said stem.

2. The yoke of claim 1 wherein each of said barb portions includes opposed inwardly converging sides, said sides of adjacent leaves defining said v-shaped slot therebetween.

3. The yoke of claim 2 wherein said opposed sides extend between about one eighth to about three fourths the length of said barb portion.

4. The yoke of claim 2 wherein said opposed sides taper at an angle of about twenty degrees.

5. A yoke for use in a medical instrument to removably secure a manipulator shaft in an associated instrument tube and to connect an end effector to said manipulator shaft, said yoke comprising a hollow stem operably coupled to and surrounding the distal end of said manipulator shaft and extending into the distal end of said instrument tube, said stem including a plurality of unitary, circumferentially and longitudinally extending spaced-apart flexible legs, each such leg including opposed inwardly converging sides which facilitate the flexing and compression of said legs when said manipulator shaft and said stem are respectively extended into and removed from said distal end of said instrument tube.

6. The yoke of claim 5 wherein each of said legs includes a wedge shaped tip terminating in a flat peripheral face and said opposed inwardly tapered sides are located on said tip.

7. The yoke of claim 6 wherein said opposed inwardly tapered sides extend between about one eighth to about three fourths the length of said tip.

8. The yoke of claim 6 wherein said opposed inwardly tapered sides taper inwardly at an angle of about twenty degrees.

9. The yoke of claim 5 wherein each of said legs includes a shoulder and a wedge shaped tip extending outwardly from said shoulder, said opposed inwardly tapered sides being located on said tip and terminating into a flat peripheral face, said shoulder on each of said legs abutting against a shoulder in the interior of said instrument tube to secure said manipulator shaft in said instrument tube.

10. The yoke of claim 9 wherein said manipulator shaft includes a distal neck having an interior circumferential cavity, said tips of said legs being wedged in said cavity to facilitate the flexing and compression of said legs so as to disengage the shoulder on each of said legs from said shoulder in said instrument tube and allow the removal of said manipulator shaft from said instrument tube.

11. A medical instrument comprising:
a) a handle member including a pivotable handle and a connector rod operably coupled to said pivotable handle for reciprocal movement in response to the pivotal movement of said handle;
b) an elongate detachable instrument tube coupled to and extending outwardly from said handle member, said instrument tube including an interior shoulder in the distal end thereof;
c) an elongate manipulator shaft extending through said instrument tube and coupled to said connector rod, said manipulator shaft being reciprocable in said instrument tube in response to the reciprocal movement of said connector rod, said manipulator shaft being detachable from said connector rod and removable from said instrument tube;
d) a yoke comprising a hollow stem operably coupled to and surrounding the distal end of said manipulator shaft and extending into the distal end of said instrument tube for removably securing said manipulator shaft in said instrument tube, said yoke including a plurality of adjacent, spaced-apart flexible legs unitary with the hollow stem and each including a wedge shaped tip for guiding said yoke into said instrument tube, each tip including a shoulder and opposed inwardly tapered sides, said sides of adjacent legs abutting each other when said yoke is extended into said instrument tube to facilitate the compression of said legs into contact with each other, said shoulder on each of said legs abutting against said interior shoulder in said distal end of said instrument tube to secure said manipulator shaft in said instrument tube; and
e) an instrument end effector operably coupled to said yoke and the distal end of said manipulator shaft and operable between selected orientations in response to the reciprocal movement of said manipulator shaft.

12. The medical instrument of claim 11 wherein said opposed inwardly tapered sides of each of said tips extend a length between about one eighth to about three fourths the length of each of said tips.

13. The medical instrument of claim 11 wherein said opposed inwardly tapered sides taper inwardly at an angle of about twenty degrees.

14. The medical instrument of claim 11 wherein said yoke includes a hollow tubular stem and a unitary distal fork, said end effector being pivotally coupled to and extending outwardly from said fork, the distal end of said manipulator shaft extending through said stem and said fork, said plurality of legs extending longitudinally and circumferentially about said stem in spaced-apart relationship.

15. The medical instrument of claim 11 wherein said manipulator shaft includes a distal neck having an interior circumferential cavity, said tips of said legs being wedged in said cavity to facilitate the flexing and compression of said legs into contact with each other to disengage the shoulder on each of said legs from said shoulder in said instrument tube and allow the removal of said manipulator shaft from said instrument tube.

16. A medical instrument comprising:
a) a handle member including a pivotable handle, a connector rod operably coupled to said pivotable handle for reciprocal movement in said handle member in response to the pivotal movement of said handle, and a knob coupled to and journalled for rotation about the distal end of said handle member, said knob including a unitary threaded stem;
b) an elongate instrument tube including a sliding collar thereon threadable onto said stem of said knob of said handle member for detachably coupling said instrument tube to said handle member, said instrument tube including an interior shoulder in the distal end thereof;
c) an elongate shaft extending through said instrument tube and coupled to said connector rod, said manipulator shaft being reciprocable in said instrument tube in response to the reciprocal movement of said connector rod, said manipulator shaft additionally being detachable from said connector rod and removable from said instrument tube;
d) a yoke coupled to and surrounding the distal end of said manipulator shaft and extending into the distal end of said instrument tube for removably securing said manipulator shaft in said instrument tube, said yoke including a fork having spaced-apart fingers and a unitary hollow cylindrical stem having a plurality of longitudinally and circumferentially extending spaced-apart flexible legs, each of said legs including a wedge shaped tip for guiding said yoke into said instrument tube, each of said tips including a shoulder and opposed inwardly tapered sides terminating in a flat peripheral face, said legs and said tapered sides of adjacent legs compressing and abutting against each other respectively when said yoke is extended into said distal end of said instrument tube and said shoulder on each of said tips abutting said shoulder in said distal end of said instrument tube for securing said manipulator shaft in said instrument tube; and
e) an instrument end effector operably coupled to the distal end of said fork of said yoke and the distal end of said manipulator shaft respectively and operable between selected orientations in response to the reciprocal movement of said manipulator shaft.

17. The medical instrument of claim 16 wherein said opposed inwardly tapered sides of each of said tips extend a length between about one eighth to about three fourths the length of each of said tips.

18. The medical instrument of claim 16 wherein said opposed inwardly tapered sides taper inwardly at an angle of about twenty degrees.

19. The yoke of claim 16 wherein said manipulator shaft includes a distal neck having an interior circumferential cavity, said tips of said legs being wedged in said cavity to facilitate the flexing and compression of said legs into contact with each other to disengage the shoulder on each of said legs from said shoulder in said instrument tube and allow the removal of said manipulator shaft from said instrument tube.

* * * * *